United States Patent [19]

Thery et al.

[11] 4,299,489
[45] Nov. 10, 1981

[54] DEVICE FOR DETERMINING THE HISTOGRAM OF SIZES OF PARTICLES

[76] Inventors: Jean-Francois Thery, 30, rue Barque, Paris, France, 75015; Henri Maitre, 27, rue Stephen Pichon, Paris, France, 75013; Jacques P. Fleuret, 61, av. Casanova, Ivry, France, 94200

[21] Appl. No.: 162,667

[22] Filed: Jun. 24, 1980

[30] Foreign Application Priority Data

Jun. 22, 1979 [FR] France ............... 79 16168

[51] Int. Cl.$^3$ ............................ G01N 15/02
[52] U.S. Cl. .................. 356/336; 350/162 SF
[58] Field of Search ............... 356/335, 336; 350/162 SF

[56] References Cited

U.S. PATENT DOCUMENTS 4,037,965 6/1977 Weiss ................... 356/336

OTHER PUBLICATIONS

Anderson, N. L. and Beissner, R. E., "Counting and Classifying Small Objects by Far-Field Light Scattering", *Applied Physics*, Jul. 1971, vol. 10, No. 7, pp. 1503-1508.

Mohandas, Bessis and Narla, *Transactions of the Academy of Sciences of Paris*, Jun. 17, 1974, vol. 278, pp. 3263-3265, and Apr. 26, 1976, vol. 282, pp.1567-1570.

"Laser Granulometer, Model 227", Compagnie Industrielle des Lasers, NC 227-5, 1978.

Leeds and Northrup Co., Microtrac (TM) Particle Size Monitor for On-Stream Dry-Powder Measurement and Control.

*Primary Examiner*—John K. Corbin
*Assistant Examiner*—Bruce Y. Arnold
*Attorney, Agent, or Firm*—Lowe, King, Price & Becker

[57] ABSTRACT

A particle size analyzer device for granular and cellular substances composed of particles having sizes lying in a given dimensional range comprises a coherent light source for illuminating a sample of the substance and means for forming the two variable Fourier transform of the sample, i.e. its bidimensional diffraction spectrum. A monodimensional portion of the bidimensional spectrum is isolated along a radius thereof determining an amplitude function versus the radial distance from the center of the spectrum. This amplitude function is processed by successively (i) computing its Hankel transform, (ii) and deriving the second derivative of the Hankel transform. This second derivative is a convolution product of the distribution function of the particle sizes by another function. The distribution function is extracted from said convolution product.

18 Claims, 7 Drawing Figures

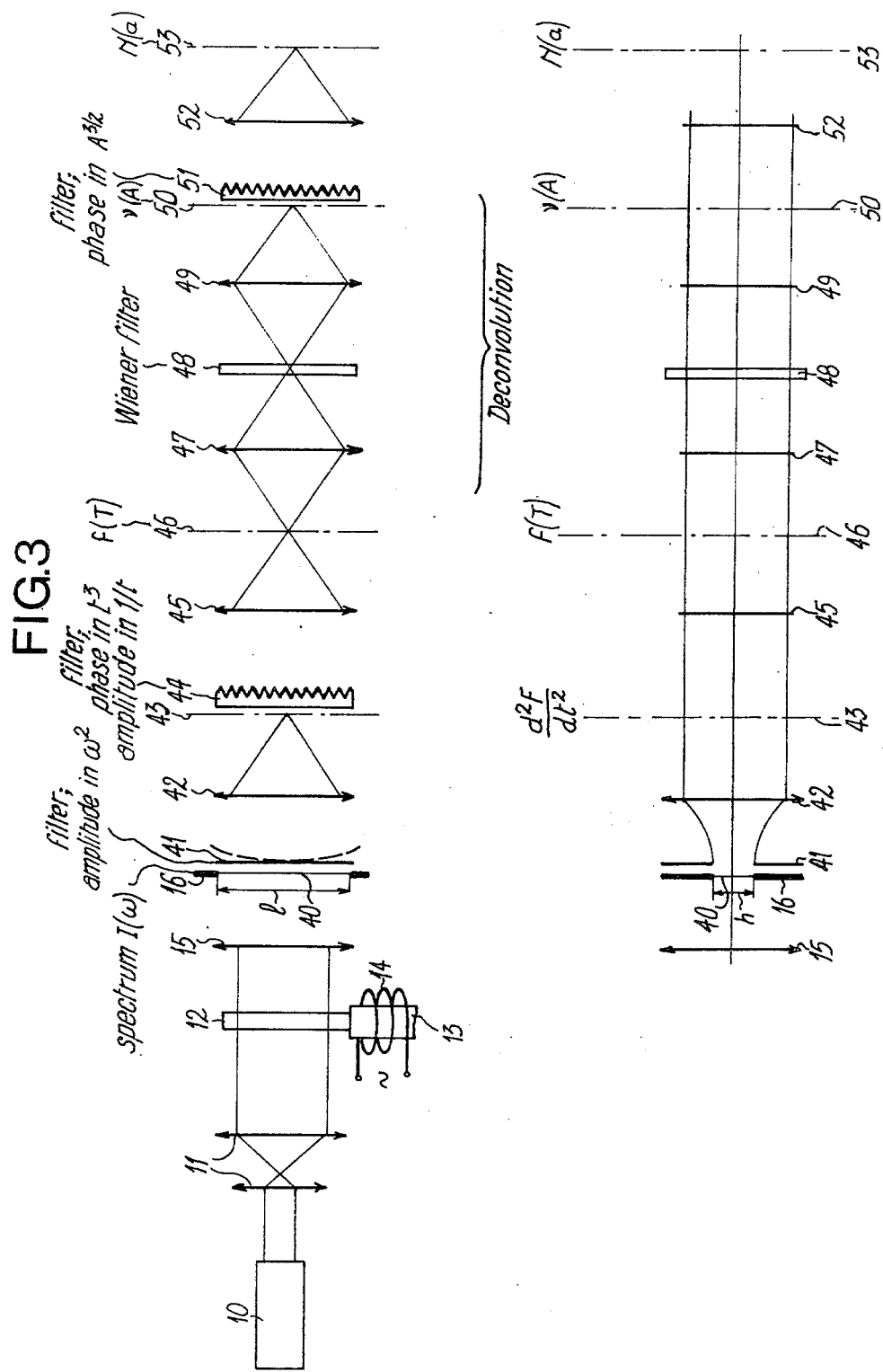

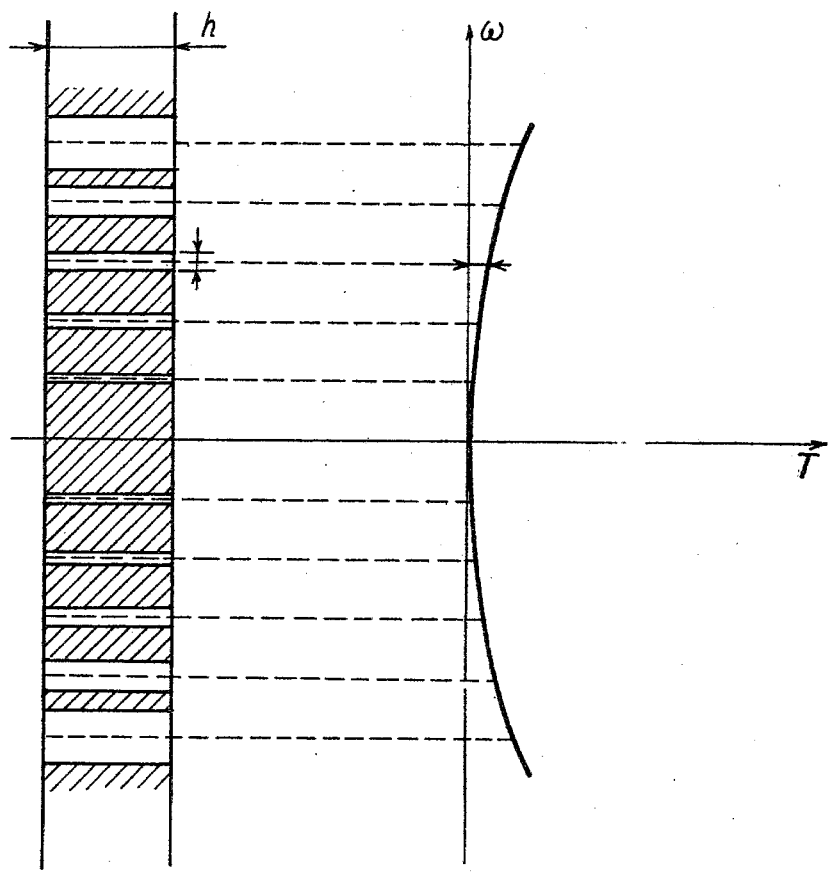

DEVICE FOR DETERMINING THE HISTOGRAM OF SIZES OF PARTICLES

BACKGROUND OF THE INVENTION

1. Field of the Invention

The present invention relates to a device for determining the histogram of a particle-size distribution for products or substances composed of particles, grains or discrete cells and, more especially, to such a device wherein a histogram is provided by analyzing a diffraction spectrum of the substance in a coherent optical system.

The device of the invention permits, in particular, a haematological analysis of blood smears or blood particles in liquid flow. It may also be employed in the granulometric study of industrial powders.

2. Description of the Prior Art

The method of analysing powders by diffraction in coherent optical systems was introduced by N. L. Anderson and R. E. Beissner in an article entitled "Counting and Classifying Small Objects by Far-Field Light Scattering", *Applied Physics*, July, 1971, Volume 10, No. 7, pages 1503–1508. This method provides an overall analysis of the sample, giving quick results with sound statistical validity. The principle thereof is as follows: the sample (powder, blood smear, cells in a liquid medium, etc) is illuminated by a laser. By taking measurements from the diffraction spectrum, the characteristics of the population under examination may be deduced.

Marcel Bessis and Narla Mohandas, *Transactions of the Academy of Sciences of Paris*, June 17, 1974, Volume 278, pages 3263–3265, and April 26, 1976, Volume 282, pages 1567–1570, were the first to employ analysis by diffraction of biological samples, with a rather particular application in mind: namely, the study of cell deformability.

Two pieces of equipment for granulometric analysis by diffraction are on the market: Compagnie Industrielle des Lasers, a French Company of 91460 Marcoussis, France, uses a laser granulometer for the study of powders, by responding to 8 measurement points on the histogram, and Leeds and Northrup Company, North Wales, PA 19454, makes a device referred to as Microtrac which responds to 13 measurement points on the histogram.

The foregoing systems and devices process a predetermined number of discrete measurements at a limited number of measurement points. Although this is suitable for industrial powders, the use of a limited number of measurement points is not usually suitable for biomedical applications where a greater resolution in the histogram is called for.

The objective of the invention is to provide a continuous histogram of the distribution of particle sizes or, at least a very high number, a thousand or more, of points of this histogram.

SUMMARY OF THE INVENTION

The present invention comprises means for illuminating a granular sample with a coherent optical source, i.e., a laser and for derives a radial recording of the diffraction spectrum obtained by means of a photodetector. Digital processing of this radial recording includes the following stages:

I. Spectral intensity measurement $$I(\omega) = 4\pi^2 \int_0^\infty a^4 \left[ \frac{J_1(ka\omega)}{ka\omega} \right]^2 N(a) da \text{ with } k = 2\pi/\lambda \quad (1)$$

II. Hankel transformation $$F(t) = \int_0^\infty I(\omega) J_0(k\omega t) \omega d\omega \quad (2)$$

III. Second derivative $$\frac{d^2F}{dt^2} = F''(t) = t \int_{t/2}^\infty \frac{N(a) da}{\sqrt{a^2 - \frac{t^2}{4}}} \quad (3)$$

IV. Deconvolution $$\frac{1}{t} \frac{d^2F}{dt^2} = \int_0^\infty g(T-A) \frac{N(\sqrt{A})}{2\sqrt{A}} dA \quad (4)$$

where:

$N(a)$ is the number of particles of radius a;

$\omega$ is the radial distance of the running point in the plane of the diffraction spectrum;

$I(\omega)$ is the intensity of light at distance $\omega$ from the center of the diffraction spectrum;

t refers to the space variable conjugate of $\omega$.

A and T are variables derived from a and t respectively, as will be seen in the mathematical part of the description. The function g is defined at a later stage (Equation 14).

Establishing equations (1), (2), (3) and (4).

Before going any further, an explanation is given of the mathematics behind the processing of a radial section of the diffraction spectrum.

Let us first consider $N(a)$ circular discs, of radius a having centers $x_i$, $y_i$ that are randomly spread, in the object plane. The diffracted complex amplitude in the Fourier plane is expressed as a function of the angular spectral coordinates (u,v) by:

$$f_{N(a)}(u,v) = S(u,v) \sum_{i=1}^{N(a)} e^{jk(x_i u + y_i v)} \quad (5)$$

where $S(u,v)$ represents the amplitude of the diffraction spectrum of a centered disc:

$$S(u,v) = 2\pi a^2 \frac{J_1(ka\omega)}{ka\omega} \quad (6)$$

$$\left( \omega = \sqrt{u^2 + v^2} \right)$$

The sum of exponential terms in (5) represents a granularity term, which expresses the rapid fluctuations in interference which are characteristic of speckle.

The intensity observed depends therefore on the positions, assumed to be randomly distributed, of all the particles. This is consequently a random-number situation, an average value of which can be obtained using conventional methods by having the positions of the particles vary per a certain probability law. Another way of obtaining this average consists, in practice, of making the whole sample vibrate and of integrating the intensity of light over a certain interval of time. In this manner, a simulation of the recording of an overall average is performed. This will be noted $\langle\ \rangle$. Use will also be made of the condensed notation: $\hat{x} = \langle x \rangle$.

In the case of a population of objects of different radii, $a_m$ (m=1,M), the recorded intensity will be:

$$\hat{I}(u,v) = \left\langle \left| \sum_{m=1}^{M} S_m(u,v)\, g_m(u,v) \right|^2 \right\rangle \qquad (7)$$

with $S_m(u,v)$ amplitude of the diffraction spectrum of a disc of radius $a_m$;

$$g_m(u,v) = \sum_{p=1}^{N_m} e^{jk(x_{p,m}u + y_{p,m}v)} \text{ granularity term}$$

$N_m$ number of objects of the class m (of radius $a_m$);
$(x_{p,m}; y_{p,m})$ coordinates of the $p^{th}$ object of the class m.

Expansion of (7) makes it possible to distinguish between the squared and crossed terms, namely:

$$\hat{I}(u,v) = \left\langle \sum_{m=1}^{M} S_m^2 |g_m|^2 \right\rangle + \left\langle \sum_{\substack{m,m' \\ m \neq m'}} S_m S_{m'} g_m g_{m'}^* \right\rangle \qquad (8)$$

where $g_{m'}^x$ is the complex conjugate of $g_{m'}$.

In the following, the statistical independence between different classes will be assumed.

In view of the quick phase fluctuations of the granularity terms, the following approximations will be assumed:

$$\begin{cases} \hat{g} \simeq 0 & (9a) \\ \widehat{|g_m|^2} \simeq N_m & (9b) \end{cases}$$

These two relationships are justified for the frequency range defined by:

$$\omega = \sqrt{u^2 + v^2} \gg \omega_o = \frac{\lambda}{L}$$

($L$ = width of the object field observed)

The final expression obtained for the intensity then becomes $$\hat{I}(u,v) \simeq \sum_{m=1}^{M} S_m^2(u,v)\, N_m \qquad (10)$$

In the case of circular objects, (10) can be written, by substituting (6)

$$\hat{I}(u,v) = I(\omega) \simeq 4\pi^2 \sum_{m=1}^{M} a_m^4 \left( \frac{J_1(k a_m \omega)}{k a_m \omega} \right)^2 N_m \qquad (11)$$

Processing the intensity $I(\omega)$.

In the case of a continuous histogram ($N_m \rightarrow N(a)da$), (11) will be written in the form of $$I(\omega) = 4\pi^2 \int_0^\infty a^4 \left( \frac{J_1(ka\omega)}{ka\omega} \right)^2 N(a)\, da \qquad (1)$$

The Hankel transformation in (1) is:

$$F(t) = \int_0^\infty I(\omega) J_0(k\omega t)\, \omega d\omega \qquad (2)$$

$$F(t) = \int_0^\infty a^4 N(a) \frac{1}{a^2} C\left[\frac{t}{2a}\right] da \qquad (12)$$

where C designates the self-correlation function of a circular disc:

$$C\left[\frac{t}{2a}\right] = \begin{cases} \text{Arc}\cos\frac{t}{2a} - \frac{t}{2a}\sqrt{1 - \frac{t^2}{4a^2}} & t < 2a \\ 0 & t \geq 2a \end{cases}$$

Let us take the second derivative of (12) under the integral sign. The second derivative gives:

$$\frac{d^2 F}{dt^2} = t \cdot \int_{t/2}^\infty \frac{N(a)\, da}{\sqrt{a^2 - \frac{t^2}{4}}} \qquad (3)$$

Equation (3) becomes a convolution equation as a result of the following change of variable:

$A = a^2$ $T = t^2/4$ and by setting $$f(T) = \frac{1}{t} \frac{d^2 F}{dt^2} \qquad (13)$$

one obtains:

$$f(T) = \int_0^\infty g(T - A) \frac{N(\sqrt{A})}{2\sqrt{A}}\, dA \qquad (4)$$

where:

$$\left. \begin{array}{ll} g(T - A) = \dfrac{1}{\sqrt{A - T}} & \text{if } T < A \\ \quad\quad\quad\quad = 0 & \text{if } T \geq A \end{array} \right\} \qquad (14)$$

It can thus be seen that $N(\sqrt{A})$ appears in the convolution Equation (4) and can be obtained by deconvolution.

To recap, the process stages are the following:

I. measurement of the intensity $I(\omega)$ of light along a radius of the spectrum;

II. Hankel transformation (it will be remembered a Hankel transformation is none other than the expression of a Fourier transformation in the case of a function with symmetry of revolution);

III. double differentiation

IV. deconvolution

BRIEF DESCRIPTION OF THE DRAWINGS

The above and still further objects, features and advantages of the present invention will become apparent upon consideration of the following detailed description of several specific embodiments thereof, especially when taken in conjunction with the accompanying drawings.

FIG. 3 is a schematic diagram of a third particle-size analyzer device in which the calculations are performed optically; and FIGS. 4A, 4B, 5A and 5B are diagrams of filters used in the device of FIG. 3.

DESCRIPTION OF THE PREFERRED EMBODIMENTS

Figure 1:
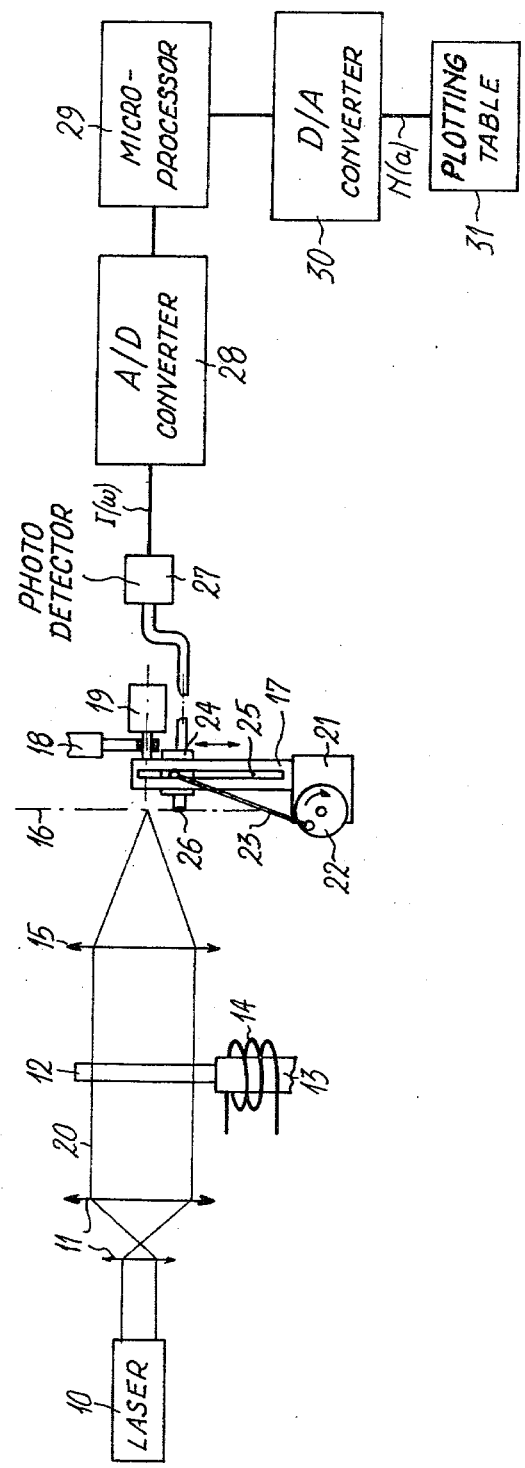
FIG. 1 is a schematic diagram of a first particle-size analyzer device in keeping with the invention giving a continuous histogram and in which the calculations are performed by a microprocessor.

In reference to FIG. 1, a coherent optical source in the form of laser 10, a He-Ne laser for instance, illuminates an afocal system 11. Beam 20 derived from laser 10 passes through sample 12 which is contained on a sample holder in the form of a microscopic plate upon which blood has been smeared. The plate containing sample 12 is secured to a vibrator including a ferromagnetic core 13 integral with the plate and a magnetizing coil 14. Core 13 and coil 14 form an assembly fed by a current of frequency 100 Hz, for example. The sample spectrum is formed on a screen 16 in the focal plane of objective 15.

Rotating arm 17 is turned by shaft attached to a base 18 and coaxial to the beam. The rotation of arm 17 is controlled by a step-by-step motor 19. Mounted on arm 17 is a motor which, by a system of rod 22 and eccentric crank 23, slides element 24 the length of a groove 25 in arm 17. Moving element 24 carries optical fibre 26 bearing a lens at an input end thereof. The output end of optical fibre 26 is connected to a photodetector 27.

The photodetector 27 produces an output signal which is representative of I ($\omega$), as defined by Equation (1). The output signal of photodetector 27 is coupled to an analog-digital converter 28, having a digital output signal coupled to a microprocessor 29. Microprocessor 29 performs the calculations associated with the Hankel transformation, the second derivative and the deconvolution, as respectively indicated by Equations (2), (3) and (4).

The digital output signal microprocessor 29, indicated by the function N (a), is coupled to digital-analog converter 30 which derives an analog signal coupled to a plotting table 31.

Figure 2:
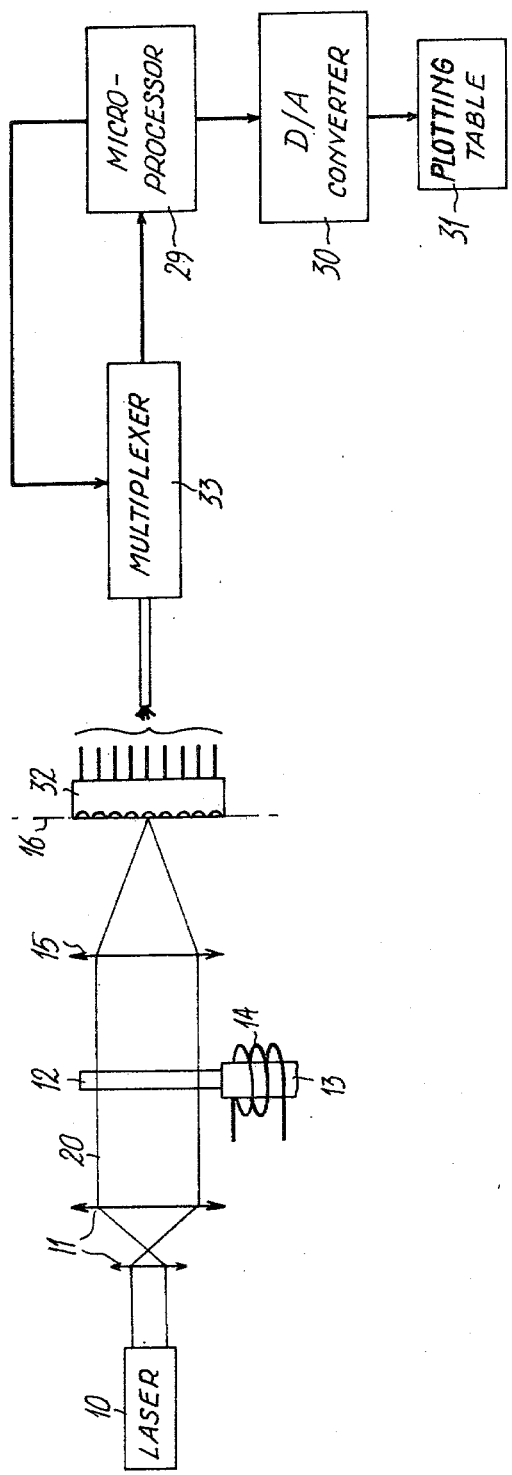
FIG. 2 is a schematic diagram of a second particle-size analyzer device in keeping with the invention enabling a discrete histogram to be obtained with a very high number of points.

In FIG. 2, elements 17 to 27 inclusive of FIG. 1 are eliminated and the spectrum I ($\omega$) incident on plane 16 is read by an elongated strip 32 of photodetectors that drives multiplexer 33. The photodetectors of strip 32 produce output signals which are time divisions multiplexed by multiplexer 33 in response to clock pulses produced by microprocessor 29.

Photodiode strips comprising a large number of photodiodes are known in the field. For example, one could use strips of the type RL 1024 Reticon strips with 1024 photodiodes or coupled charge devices CCD 131 with 1024 elements or type CCD 121 with 1078 elements manufactured by Fairchild.

In FIG. 3, the Hankel transformation, the second derivative and the deconvolution are achieved optically.

Reference numbers 10, 11, 12, 13–14, 15 and 16 have the same significance as in FIGS. 1 and 2 and respectively designate the laser, the afocal system, the sample, the objective and the focal plane of the objective. The spectrum I ($\omega$) is obtained in plane 16. A radial slit is placed in plane 16 to isolate the radial monodimensional variation of the spectral intensity.

(I) Optical production of the second derivative

An $\omega^2$ mono-dimensional filter 41 is located in plane 16; filter 41 has transmittance proportional to $\omega^2$. The height h of filter 41 is very small, compared to its width l. The second derivative $d^2F/dt^2$ is obtained in plane 43 due to lens 42. Beyond lens 42, optical processes on the beam are monodimensional, whereby all lenses beyond lens 42 are cylindrical. In FIG. 3, lens 42 is spherocylindrical and produces a one dimension Fourier transformation and simply enlarges the dimension corresponding to height h of the slit. Due to the properties of symmetry, this processing structure is approximately equivalent to the direct use of a Hankel transform.

(II) Optical production of the change of variable t→T

As disclosed by O. Bryngdahl (Optics Communication v. 10, no. 2, February 1974, page 164), it is possible to change an optical variable by positioning a phase filter on the object to be transformed, and an objective used in a Fourier transformation. Filter 44 is therefore placed in plane 43. The phase of filter 44 is calculated depending on the transformation to be performed. In this case, according to Bryngdahl, the phase of the transforming filter must satisfy:

$$\frac{d\phi}{dt} = \frac{2\pi}{\lambda f} \times T = \frac{\pi}{2\lambda f} t^2$$

It turns out from this that $\phi$ is proportioned to $t^3$ modulo $2\pi$.

Moreover, according to Equation (13), $d^2F/dt^2$ must to be attenuated by a function of $1/t$. Complex monodimensional filter 44 must have:
- an amplitude of $1/t$
- a phase proportional to $t^3$ (modulo $2\pi$).

The function f(T) is obtained in plane 46.

III. Optical production of the deconvolution by double diffraction

The deconvolution of (4) is achieved by double Fourier transformation, achieved with a Wiener filter 48 (C. W. Helstrom, Journal of Optical Society of America, 57, 3, 1967, p. 297), the transmittance of which depends on:
- the Fourier transformation of the convoluant function: $\tilde{g}$
- the signal to noise ratio of the optical processing chain (designated by $\phi$) namely:

$$\frac{1}{\tilde{g} + \frac{\phi}{g}} \qquad (15)$$

In FIG. 3, the deconvolution corresponds to two cylindrical optical systems 47 and 49. The function $$(A) = \frac{N(\sqrt{A})}{2\sqrt{A}}$$

is obtained in plane 50.

IV. Optical production of the change of variable A→a

This last change of variable is achieved by placing filter 51, similar to filter 44, in plane so the phase of filter S 1 is such that:

$$\frac{d\phi}{dA} = \frac{2\pi}{\lambda f} \times a = \frac{2\pi}{\lambda f} \sqrt{A}$$

Thereby $\phi$ is proportional to $A^{3/2}$ (modulo $2\pi$).

Optical system 52 provides the desired histogram N (a) in plane 53. Histogram N (a) is analysed (so it can be finally drawn on a plotting table) by a sweeping and photodetecting system of the same type as described in connection with FIGS. 1 and 2.

V. Synthesis of the filters

Figure 5A:
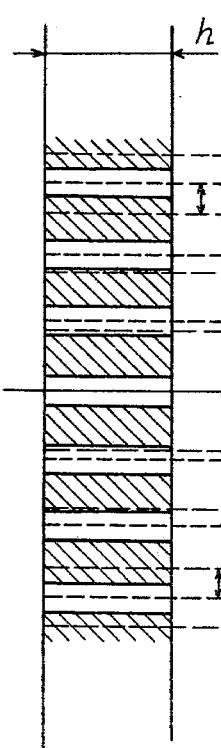
Figure 5B:
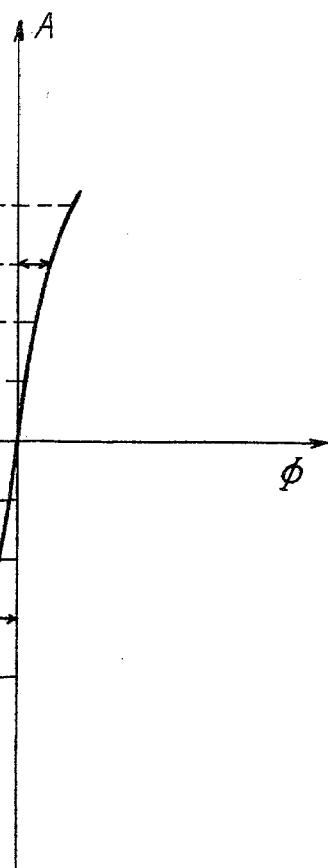

The filters 41, 44, 48 and 51 are implemented by the classical means of computed holography (A. W. Lohmann, D. P. Paris, Appl. Opt. 1967, 5, 1739) which allow the realization of a complex function on a real frame by adequate coding of the desired amplitude and phase. For each filter, the complex function to be represented is sampled. Each sample corresponds to each complex value to be represented. To derive each sample, there is provided a binary cell or "slit" having an aperture proportional to the amplitude, of the cell value. The relative shift in position of the slits is proportional to the phase shift introduced by the filter. The kind of pattern obtained for the amplitude filter 41 is illustrated on FIGS. 4A and 4B. The corresponding pattern, in the case of the phase filter 51, is illustrated in FIGS. 5A and 5B. For the filters 44 and 48, which are complex filters, the cells or "slits" have, at the same time, amplitude related apertures and phase related shifts. In the particular case of filter 48, the complex function (15) results from Fourier transformation of relationship (14) by a computer. The filter generation uses classical means for graphical drawing and photoreduction.

While there have been described and illustrated several specific embodiments of the invention, it will be clear that variations in the details of the embodiments specifically illustrated and described may be made without departing from the true spirit and scope of the invention as defined in the appended claims.

What we claim is:

1. A particle size analyzer device for granular and cellular substances composed of particles having sizes lying in a given range, said device comprising:
   a coherent light source;
   a sample of said substance;
   means for forming the Fourier transform of said sample and thereby obtaining the bidimensional diffraction spectrum of the sample;
   means for isolating that part of said bidimensional diffraction spectrum lying along a radius of the same and thereby forming a radially directed monodimensional spectrum;
   means for sensing a first signal equal to the amplitude of said monodimensional spectrum versus the distance $\omega$ from an origin point thereof;
   means for forming the Hankel transform of said first signal and thereby obtaining a second signal;
   means for taking the second derivative with respect to "t", where "t" is the space variable conjugate of "$\omega$", thereby obtaining a third signal equal to the convolution product of the distribution function of the particle sizes by another function of said particle size;
   means for extracting from said convolution product said distribution function; and
   means for displaying said distribution function versus the size of the particles of the substance.

2. The particle size analyzer device as set forth in claim 1 wherein the means for sensing a first signal equal to the amplitude of the monodimensional spectrum versus distance comprises a photodetector and means for displacing said photodetector along a radius of said bidimensional spectrum.

3. The particle size analyzer device as set forth in claim 1 wherein the means for sensing a first signal equal to the amplitude of the monodimensional spectrum comprises an elongated multiphotodetector strip directed along a radius of the bidimensional spectrum and means for sequentially activating the photodetectors of the strip.

4. The particle size analyzer device as set forth in claim 1 further comprising means for vibrating the sample of the substance.

5. The particle size analyzer device for granular and cellular substances composed of particles having sizes lying in a given dimensional range, said device comprising:
   a coherent light source;
   a sample of said substance;
   means for vibrating said sample;
   means for forming the bidimensional diffraction spectrum of said sample and for isolating a monodimensional spectrum along a radius of said bidimensional spectrum;
   means for optically forming the Hankel transform of said isolated monodimensional spectrum;
   a first optical filter in the plane of the monodimensional Hankel spectrum transform having a transmittance proportional to the square of the radial distance $\omega$ to the center of said filter, whereby said first optical filter takes the second derivative with respect to "t", where "t" is the space variable conjugate of $\omega$, of the coherent wave from said source passing through said first filter;
   a second optical filter implementing a first change of variable in the size distribution function, said optical filter having a transmittance which varies as $1/r$ and a phase which varies as $r^3$, where r is the radial distance from the origin point of the filter;
   a third optical filter implementing a second change of variable in the size of distribution function, said optical filter having a transmittance which varies as $r^{3/2}$, where r is the radial distance from the origin point of the filter, whereby the coherent wave from said source passing through said second and third filters has an amplitude equal to the convolution product of the distribution function of the particle sizes by another function of said particle size;

means for extracting from said convolution product said distribution function; and means for displaying said distribution function versus the size of the particles of the substance.

6. A particle size analyzer device for granular and cellular substances composed of particles having sizes lying in a given dimensional range, said device comprising:

a coherent optical source for deriving a beam adapted to be incident on a sample of the substance;

means responsive to the beam of said source incident on the sample for forming a bidimensional diffraction spectrum of the sample, the bidimensional diffraction spectrum including a radial segment;

means responsive to the bidimensional diffraction spectrum for isolating the radial segment and for thereby forming a radially directed monodimensional spectrum;

means responsive to the monodimensional spectrum deriving a first signal having an amplitude directly proportional to the amplitude of said monodimensional spectrum versus the distance $\omega$ from an origin point thereof;

means responsive to the first signal for forming the Hankel transform of said first signal to thereby derive a second signal;

means responsive to the second signal for taking the second derivative with respect to "t" of the Hankel transform, where "t" is a space variable conjugate of "$\omega$", for thereby deriving a third signal proportional to the convolution product of the distribution function of the particle sizes and another function of said particle size;

means responsive to the third signal for extracting said distribution function from said convolution product; and means for displaying the extracted distribution function versus the size of the particles of the substance.

7. The particle size analyzer device of claim 6 wherein the means for deriving a first signal proportional to the amplitude of the monodimensional spectrum versus distance comprises a photodetector, and means for displacing said photodetector along a radius of said bidimensional spectrum.

8. The particle size analyzer device of claim 6 wherein the means for deriving the first signal proportional to the amplitude of the monodimensional spectrum comprises an elongated multiphotodetector strip radially directed along the bidimensional spectrum, and means for sequentially activating the photodetectors of the strip.

9. The particle size analyzer device of claim 6, 7 or 8 further comprising a holder for the sample, and means for vibrating the holder for the sample.

10. A particle size analyzer device for granular and cellular substances composed of particles having sizes lying in a given dimensional range, said device comprising:

a coherent optical source for deriving a beam having a longitudinal axis;

a holder for a sample of said substance in the path of a beam of the source;

means for vibrating said holder for the sample;

means responsive to the beam of said source incident on the sample for forming a bidimensional diffraction spectrum of said sample and for isolating a radial monodimensional spectrum along said bidimensional spectrum;

means responsive to the radial monodimensional spectrum for optically forming the Hankel transform of said isolated monodimensional spectrum;

a first optical filter in the plane of the formed monodimensional Hankel spectrum transform having a transmittance proportional to the square of the radial distance $\omega$ to the axis of the beam, whereby said first optical filter derives an optical response indicative of the second derivative with respect to "t" of the coherent beam from said source passing through said first filter, where "t" is a space variable conjugate of $\omega$;

a second optical filter in the path of the beam for implementing a first change of variable in a size distribution function, said optical filter having a transmittance which varies as $1/r$ and a phase which varies as $r_1^3$, where $r_1$ is the radial distance from the axis of the beam to a point on the second filter;

a third optical filter in the path of the beam for implementing a second change of variable in the size distribution function, said optical filter having a transmittance which varies as $r_2^{3/2}$, where $r_2$ is the radial distance from the beam to a point on the third filter, whereby the coherent wave from said source passing through said second and third filter has an amplitude proportional to the convolution product of the distribution function of the particle sizes and another function of said particle size;

means for extracting said distribution functions from said convolution product; and means responsive to the extracting means for displaying said distribution function versus the size of the particles of the substance.

11. A particle size analyzer device for granular and cellular substances composed of particles having sizes lying in a given dimensional range; said device comprising:

a coherent optical source for deriving a beam adapted to be incident on a sample of the substance;

means responsive to the beam of said source incident on the sample for forming a Fourier transform of said sample and for thereby deriving a bidimensional diffraction spectrum of the sample, the bidimensional diffraction spectrum including a radial segment;

means responsive to the bidimensional diffraction spectrum for isolating the radial segment and for thereby forming a radially directed monodimensional spectrum;

means responsive to the monodimensional spectrum for deriving a response indicative of the convolution product of the distribution function of the particle sizes and another function of said particle size; and means responsive to the response for extracting said distribution function from said convolution product.

12. The particle size analyzer device of claim 11 wherein the means for deriving the response includes computer means.

13. The particle size analyzer device of claim 12 wherein the computer means is a digital computer.

14. The particle size analyzer device of claim 11 wherein the means for deriving the response includes optical filter means having slits for providing predetermined amplitude and phase variations of the optical beam incident thereon as a function of beam position.

15. The particle size analyzer device of claim 11, 12 or 13 wherein the response deriving means comprises a photodetector, and means for displacing said photodetector along a radius of said bidimensional spectrum.

16. The particle size analyzer device of claim 11, 12 or 13 wherein the response deriving means comprises an elongated multiphotodetector strip radially directed along the bidimensional spectrum, and means for sequentially activating the photodetectors of the strip.

17. The particle size analyzer device of claim 11, 12, 13 or 14 further comprising a holder for the sample, and means for vibrating the holder for the sample.

18. The particle size analyzer device of claim 11, 12, 13 or 14 further including means responsive to the extracting means for displaying said distribution function versus the size of the particles of the substance.

* * * * *